(12) United States Patent
Poss et al.

(10) Patent No.: US 8,901,360 B2
(45) Date of Patent: Dec. 2, 2014

(54) PROCESS FOR CIS 1,1,1,4,4,4-HEXAFLUORO-2-BUTENE

(75) Inventors: Andrew Joseph Poss, Kenmore, NY (US); David Nalewajek, West Seneca, NY (US); Haridasan K. Nair, Williamsville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 314 days.

(21) Appl. No.: 13/110,979

(22) Filed: May 19, 2011

(65) Prior Publication Data

US 2011/0288346 A1 Nov. 24, 2011

Related U.S. Application Data

(60) Provisional application No. 61/347,134, filed on May 21, 2010.

(51) Int. Cl.
| | | |
|---|---|---|
| C07C 21/18 | (2006.01) | |
| C07C 17/278 | (2006.01) | |
| C07C 17/04 | (2006.01) | |
| C07C 17/20 | (2006.01) | |
| C07C 17/23 | (2006.01) | |
| C07C 17/25 | (2006.01) | |
| C07C 17/354 | (2006.01) | |

(52) U.S. Cl.
CPC ............ *C07C 17/278* (2013.01); *C07C 17/04* (2013.01); *C07C 17/206* (2013.01); *C07C 17/23* (2013.01); *C07C 17/25* (2013.01); *C07C 17/354* (2013.01)
USPC ............ 570/154; 570/153; 570/155; 570/231

(58) Field of Classification Search
CPC .......... C07C 17/25; C07C 17/00; C07C 41/24
USPC .................. 570/153, 154, 231, 155
See application file for complete search history.

(56) References Cited

U.S. PATENT DOCUMENTS

| | | | |
|---|---|---|---|
| 5,210,340 A | 5/1993 | Bielefeldt et al. | |
| 5,463,150 A | 10/1995 | Lui et al. | |
| 5,516,951 A | 5/1996 | Aoyama | |
| 5,608,128 A | 3/1997 | Nakada et al. | |
| 5,792,893 A * | 8/1998 | Wilson et al. | 570/257 |
| 5,969,197 A | 10/1999 | Lui et al. | |
| 6,023,004 A * | 2/2000 | Thenappan et al. | 570/188 |
| 6,399,840 B1 | 6/2002 | Schoebrechts et al. | |
| 2008/0269532 A1 * | 10/2008 | Swearingen | 570/175 |
| 2009/0156869 A1 | 6/2009 | Nappa | |

FOREIGN PATENT DOCUMENTS

| | | |
|---|---|---|
| JP | 2010001244 A | 1/2010 |
| WO | 2007059468 A1 | 5/2007 |
| WO | 2009117458 A2 | 9/2009 |
| WO | 2010014548 A2 | 2/2010 |

OTHER PUBLICATIONS

Angelini, G., et al., Synthesis and tritium-induced fluorine-19 NMR shifts of 1,1,1,4,4,4-hexafluoro-2,3-ditritio-2-butene, Canadian Journal of Chemistry, 1992, pp. 1221-1228, vol. 70, No. 4, Ist. Chim. Nucl., CNR, Rome, Italy.

* cited by examiner

*Primary Examiner* — Sudhakar Katakam
*Assistant Examiner* — Pancham Bakshi
(74) *Attorney, Agent, or Firm* — Erika S. Wilson

(57) ABSTRACT

Disclosed is a process for preparing cis-1,1,1,4,4,4-hexafluorobutene comprising the steps of (a) reacting $CCl_4$ with a compound having the formula $CF_3CX{=}CXH$, where each X is independently halogen or hydrogen, to form a compound having the formula $CF_3CXClCXHCCl_3$; (b) fluorinating the compound formed in step (a) to form a compound having the formula $CF_3CXHCXHCF_3$; (c) converting the compound formed in step (b) by a reaction selected from the group consisting of dehydrohalogenation, dehalogenation and both reactions, to form a compound having the formula $CF_3C{\equiv}CCF_3$; and (d) catalytically reducing the compound formed in step (c) with hydrogen to form the compound having the formula:

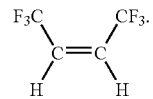

10 Claims, No Drawings

PROCESS FOR CIS 1,1,1,4,4,4-HEXAFLUORO-2-BUTENE

CROSS-REFERENCE TO RELATED APPLICATION

This application claims domestic priority from commonly owned U.S. Provisional Patent Application Ser. No. 61/347,134, filed 21 May 2010, the disclosure of which is hereby incorporated herein by reference.

BACKGROUND OF THE INVENTION

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials (GWP) associated therewith, it is desirable to use fluids having the lowest possible greenhouse warming potential in addition to zero ozone depletion potential (ODP). Thus there is considerable interest in developing environmentally friendlier materials for the applications mentioned above.

Fluorinated butenes having zero ozone depletion and low global warming potential have been identified as potentially filling this need. However, the toxicity, boiling point, and other physical properties in this class of chemicals vary greatly from isomer to isomer.

One fluorobutene having valuable properties is cis-1,1,1,4,4,4-hexafluorobutene. Thus, there is a need for new manufacturing processes for the production of hexafluorobutenes and in particular cis-1,1,1,4,4,4-hexafluorobutene:

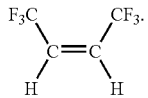

There are several methods for producing hexafluoro-2-butene, but such processes may give exclusively the trans-isomer. See, for example, the zinc reduction of 1,1,1,4,4,4-hexafluoro-2-iodobutene; K. Leedham and R. N. Hazeldine, J. Chem. Soc., 1954, 1634.

Processes that give a mixture of cis- and trans-isomers are likewise undesirable if a substantial proportion of the trans-isomer is formed. One reason is that the difference in boiling points for the two isomers is large (the trans-isomer boiling at about 9° C. and the cis-isomer boiling at about 32° C.). For applications that depend in large part on the boiling point of the fluorocarbon, the large difference in boiling points may mean that only one isomer is suitable and the other isomer therefore represents a yield loss. Another reason such a mixture is undesirable is that a good means for recycling the undesired trans-isomer is lacking. Ideally, a suitable process will provide the cis:trans isomers in a ratio of 10:1 or better.

Still other processes for cis-olefins suffer from co-production of the corresponding alkane. In the present case, this means the co-production of 1,1,1,4,4,4-hexafluorobutane. This is likewise undesirable because it does not posses the low GWP that the corresponding butene does. Furthermore, like the trans-isomer, there is no convenient way to recycle this by-product.

One prior art method for making cis-1,1,1,4,4,4-hexafluorobutene (J. Am. Chem. Soc., 1949, 71, 298) involves reduction of hexafluoro-2-butyne with hydrogen (100 atmospheres) using Raney nickel catalyst at room temperature. Not only does this pressure require specialized equipment, but the conversion was only 82% and the product was a mixture of cis-hexafluoro-2-butene (41% yield) and hexafluorobutane (25% yield). Ideally the amount of over-reduced material should be less than 10%. Still more preferably, the total amount of trans-isomer and butane are together less than 10%.

R. N. Hazeldine, J. Chem. Soc., 1952, pp. 2504, also reported the reduction of hexafluorobutyne with Raney nickel at 60° C. and 15 atmospheres of hydrogen pressure to give cis-hexafluorobutene. Although some over-reduction to hexafluorobutane was mentioned, the yield of 91% is substantially better than the yield given in the reference cited above.

A few methods exist for the exclusive preparation of non-fluorinated cis-olefins to the exclusion of the corresponding trans-isomer. The most common of these is the catalytic reduction of alkynes. A number of catalysts may be employed for this transformation but they can, unfortunately, give a wide range of results and undesirable side reactions such as over-reduction to alkanes, formation of trans-olefins, and isomerization of cis to trans olefins. In addition, a wide range of variables can alter the results, such as temperature, mixing rate, solvent, and added reagents which may intentionally or unintentionally alter the reactivity of the catalyst.

For a general discussion of this chemistry see, P. N. Rylander, Catalytic Hydrogenation over Platinum Metals, Chapter 4, Academic Press, 1967. For example, depending on the temperature, the reduction of acetylene dicarboxylic acid using Pd on BaSO$_4$ can give either succinic acid (no double bond) at −18° C. or maleic acid (cis double bond) at 100° C., while the ratios of cis to trans products for the reduction of p-methoxy-phenylacetylene carboxylic acid with the same catalyst were similar (20%±5% trans isomer) over a wide temperature range. See, S. Takei and M. Ono, Nippon Nogei Kagaku Kaisi 18 (1942b) 119.

Catalysts that have been used for the selective reduction of non-fluorinated alkynes to alkenes include Pd/C, Pd/BaSO$_4$, Pd/BaCO$_3$, and Pd/CaCO$_3$. In order to achieve high selectivity, however, the use of quinoline as a catalyst modifier has been recommended whether the catalyst is Pd/C, Pd/BaSO$_4$, or Lindlar catalyst, Pd/CaCO$_3$/Pb. See, M. Hudlicky, Reductions in Organic Chemistry, 2nd Ed., ACS Monograph 188, 1996, p 8.

The Lindlar catalyst is probably the most common one used for the reduction of hydrocarbon alkynes to cis-alkenes, modified further by the addition of an aromatic amine such as quinoline or pyridine. The amines, while often useful in improving reaction selectivity, are not desirable from the standpoint of their toxicity. The quality of the quinoline used may also affect the outcome. The Pd/CaCO$_3$/Pb catalyst, modified with pyridine, was successfully used in the reduction of an alkyne bearing a single fluorine on the carbon adjacent to the triple bond to give the corresponding cis-alkene. See, M. Prakesch, D. Gree, and R. Gree, J. Org. Chem., 66 (2001) 3146. In addition, selective hydrogenation catalyst, such as NanoSelect LF catalyst (obtained from Strem/BASF) may be used to reduce the hexafluorobutyne to the desired cis hexafluoro-2-butene.

As is well known in the art, however, fluorocarbons often behave quite differently compared to non-fluorinated alkanes, and perfluorinated compounds may behave quite differently than even partially fluorinated compounds of similar structure.

SUMMARY OF THE INVENTION

One embodiment of the present invention is a process for preparing cis-1,1,1,4,4,4-hexafluoropropene comprising the steps:

(a) reacting $CCl_4$ with a compound having the formula:

$$CF_3CX=CXH$$

where each X is independently halogen or hydrogen, to form a compound having the formula:

$$CF_3CXClCXHCCl_3$$

(b) fluorinating the compound of the formed in step (a) to form a compound having the formula:

$$CF_3CXHCXHCF_3$$

(c) converting the compound formed in step (b) by a reaction selected from the group consisting of dehydrohalogenation, dehalogenation and both reactions, to form a compound having the formula:

$$CF_3C\equiv CCF_3$$

and (d) catalytically reducing the compound formed in step (c) with hydrogen to form the compound having the formula:

$$cis\text{-}CF_3CH=CHCF_3.$$

DETAILED DESCRIPTION OF THE INVENTION

The first step of the process involves the addition of $CCl_4$ across the double bond of fluoroolefin of Formula I:

$$CF_3CX=CXH \tag{I}$$

where each X is independently either a halogen or hydrogen, to afford the saturated compound of Formula II:

$$CF_3CXClCXHCCl_3 \tag{II}$$

This reaction (Reaction No. 1) is depicted below:

$$CF_3CX=CXH+CCl_4 \rightarrow CF_3CXClCXHCCl_3$$
$$(X=\text{halogen or H}) \tag{1}$$

Typical compounds of Formula I include $CF_3CCl=CClH$, $CF_3CH=CHCl$, $CF_3CCl=CH_2$, $CF_3CCl=CFH$, $CF_3CF=CHCl$, $CF_3CF=CFH$, $CF_3CH=CFH$, $CF_3CF=CH_2$, $CF_3CH=CFH$, $CF_3CH=CHBr$, $CF_3CBr=CH_2$, $CF_3Br=CHBr$, $CF_3CH=CHI$, $CF_3CI=CHI$, $CF_3CI=CH_2$, and the like.

Typically the addition of $CCl_4$ to the olefin of Formula I can be conducted in acetonitrile with $CuCl_2$ at an elevated temperature of from 100° C. to 150° C. for a period of about 15 hours as described in J. Fluorine Chem., 1992, 56, 153. After cooling the reactor, the solvent can be evaporated and the residue containing the saturated product of Formula II extracted in a solvent washed with water and dried. Further purification can be accomplished by distillation.

In the second step the saturated compound is fluorinated with HF as shown below in Reaction No. 2:

$$CF_3CXClCXHCCl_3+3HF \rightarrow CF_3CXClCXHCF_3+3HCl \tag{2}$$

The fluorination in Reaction No. 2 can be accomplished by procedures in liquid or vapor phase by many reported procedures; see, for example, U.S. Pat. Nos. 6,689,924, 6,023,004, or 7,071,368. Although some amounts of over fluorinated compounds such as $CF_3CXFCXHCF_3$ or $CF_3CF_2CXHCF_3$ can be formed, reaction conditions are optimized such that the major compound formed on fluorination is as depicted in Reaction No. 2. By-products formation can be reduced by judicious selection of reactants ratio and conditions.

The continuous vapor phase fluorination of $CF_3CXClCXHCCl_3$ with HF and $Cr_2O_3/Al_2O_3$ catalyst system can also be carried out, for example, as described in WO 9711043 A1.

The saturated compound thus formed is then subjected to dehydrohalogenation followed by dehalogenation; well known procedures can be found in Chemistry of Organic Fluorine Compounds, 2nd Edition, pages 488-495, by M. Hudlicky. As shown below for Reaction No. 3, depending on the substituent X, dehydrohalogenation, dehalogenation or both reactions, may be employed.

$$CF_3CXClCXHCF_3 \rightarrow CF_3CX=CXCF_3+HCl \tag{3}$$

$$CF_3CX=CXCF_3+Zn \rightarrow CF_3C\equiv CCF_3+ZnX_2 \text{ (for } X=Cl, Br, I)) \tag{3}$$

In addition, when X=H, an additional steps of adding $Cl_2$ and subsequent dehalogenations are necessary to afford $CF_3C\equiv CF_3$ as depicted in Reactions 3a and 3b:

$$CF_3CH=CHCF_3+Cl_2 \rightarrow CF_3CHClCHClCF_3 \tag{3a}$$

$$CF_3CHClCHClCF_3 \rightarrow CF_3C\equiv CCF_3+2HCl \tag{3b}$$

The liquid phase dehydrohalogenation can be conducted with a base such as aqueous NaOH, KOH and the like, preferably in the presence of a phase transfer catalyst such as tetralkylammonium chloride, crown ethers and the like, as described in U.S. Pat. No. 6,548,719.

Dehalogenation can be conducted by a heating halo compound with Zn metal in a solvent such as acetic anhydride or dioxane at elevated temperature. See, J. Amer. Chem. Soc. 1949, 71, 298; and J. Am. Chem. Soc. 1961, 83, 3424.

Reduction of $CF_3C\equiv CCF_3$ with hydrogen to cis-$CF_3CH=CHCF_3$ can be done using Lindlar catalyst, and the other catalysts described above.

The following examples are provided to further illustrate the invention and should not be taken as limitations of the invention.

EXAMPLE 1

Addition of $CCl_4$ to $CF_3CCl=CHCl$

In to a 1 Liter clean, dry stainless steel Parr Reactor was added $CCl_4$ (154 g, 1.0 mol), followed by $CuCl_2$ (1.35 g, 0.01 mol) and acetonitrile (50 mL). The reactor was closed, cooled to −20° C. and $CF_3CCl=CHCl$ (124 g, 0.75 mol) was introduced as a liquid at about 0° C. The content in the reactor was heated to maintain a temperature of from 130° C. to 140° C. for 16 hours. After cooling to room temperature (about 20° C.), more volatile materials were evaporated and the residue was washed with 1M HCl (50 mL) and water (2×100 mL) and dried ($MgSO_4$). The product was distilled to afford 185 g (77%) $CF_3CCl_2CHClCCl_3$.

In a similar manner, the reaction was conducted as above except that $CF_3CCl=CFH$ was used as the starting material instead of $CF_3CCl=CHCl$ to afford $CF_3CCl_2CFHCCl_3$ in 80% yield.

EXAMPLE 2

Fluorination of $CF_3CCL_2CHCCC_3$

To a 1 Liter autoclave/Parr reactor was charged $SbCl_5$ (25 g) and $CF_3CCl_2CHClCCl_3$ (200 g, 0.63 mol) under a nitrogen atmosphere. The reactor was cooled to 0° C. and anhydrous HF (120 g) was condensed and added to the reactor. The contents of the autoclave were heated to and maintained at a temperature of from 90° C. to 100° C. with agitation for 1 hour. As the reaction proceeded an increase in pressure was observed. The reactor was cooled to about 20° C. and vented to cold traps. The product in the autoclave was washed with water and caustic solution to afford $CF_3CCl_2CHClCF_3$ (119 g, 70% yield).

The above reaction was conducted in the same manner except that $CF_3CCl_2CFHCCl_3$ was used instead of $CF_3CCl_2CHClCCl_3$ as the starting material to afford 75% yield of $CF_3CHClCFHCF_3$.

Vapor phase fluorination of $CF_3CCl_2CHClCCl_3$ with $Cr_2O_3/Al_2O_3$ catalyst was conducted in a similar manner as described in Examples 3-6 of WO 9711043 A1. A 60% to 80% conversion of $CF_3CCl_2CHClCCl_3$ to $CF_3CCl_2CHClCF_3$ was observed.

EXAMPLE 3

Dehydrohalogenation of $CF_3CCl_2CHClCF_3$

To a 500 ml aqueous solution of KOH (20 wt %) containing a phase transfer catalyst (Aliquat 336, 1.5 mmol) at about 0° C. in an autoclave was added $CF_3CCl_2CHClCF_3$ (0.2 mol) and stirred for 2 hours. Analysis of the volatile material by gas chromatography indicated the main product as $CF_3CCl=CClCF_3$. Further purification was achieved by distillation

EXAMPLE 4

Dehalogenation of $CF_3CCl=CClCF_3$

Into a 1 Liter flask fitted with a stirrer, a dropping funnel and condenser with an outlet to a cooled trap was charged with Zn dust (40 g, 0.62 mol), acetic anhydride (120 mL) and heated to a temperature range of 130° C. to 135° C. To this heated solution was added a solution of $CF_3CCl=CClCF_3$ (56 g, 0.24 mol) in 40 mL acetic anhydride over a period of 4 hours. The product $CF_3C \equiv CCF_3$ was removed continuously in a cold trap (−78° C.).

EXAMPLE 5

Reduction of $CF_3C \equiv CCF_3$ to cis-$CF_3CH=CHCF_3$

A 1 L clean, dry autoclave was charged with 3.0 g catalyst (5% Pd on $CaCO_3$ poisoned with 3.5% lead) and 240 mL ethanol. The content in the autoclave was cooled to −78° C. and air inside the reactor was removed by purging with nitrogen after evacuating; this was repeated twice. After this 48 g $CF_3C \equiv CCF_3$ was condensed and the contents were brought to room temperature. Hydrogen was added such a way that the pressure in the reactor was maintained below about 90 psi and stirred for 20 hours at temperature range of 25° C. to 30° C. The content in the autoclave was cooled (−78° C.), and $H_2$ gas was vented. The material in the autoclave was distilled to afford cis-$CF_3CH=CHCF_3$ (42 g, 86% yield). Further purification can be accomplished via distillation at 30° C. to 32° C.

In a similar manner, the reaction was carried as above except for the fact that NanoSelect LF 100 or NanoSelect LF 200 (Strem Chemicals, Inc.) catalyst was used instead 5% Pd on $CaCO_3$ poisoned with 3.5% lead to afford 60% yield of cis-$CF_3CH=CHCF_3$.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for preparing cis-1,1,1,4,4,4-hexafluorobutene comprising steps:
    (a) reacting $CCl_4$ with a compound having the formula:

$$CF_3CX=CXH$$

where X=halogen or H independent of each other, wherein the compound $CF_3CX=CXH$ is selected from the group consisting of $CF_3CCl=CClH$, $CF_3CH=CHCl$, $CF_3CCl=CH_2$, $CF_3CCl=CFH$, $CF_3CF=CHCl$, $CF_3CF=CFH$, $CF_3CH=CFH$, $CF_3CF=CH_2$, $CF_3CH=CFH$, $CF_3CH=CHBr$, $CF_3CBr=CH_2$, $CF_3CBr=CHBr$, $CF_3CH=CHI$, $CF_3CI=CHI$, and $CF_3CI=CH_2$; to form a compound having the formula:

$$CF_3CXClCXHCCl_3$$

(b) fluorinating the compound formed in step (a) to form a compound having the formula:

$$CF_3CXHCXHCF_3$$

(c) converting the compound formed in step (b) by a reaction selected from the group consisting of dehydrohalogenation, dehalogenation and both reactions, to form a compound having the formula:

$$CF_3C \equiv CCF_3$$

and
    (d) catalytically reducing the compound formed in step (c) with hydrogen to form the compound having the formula:

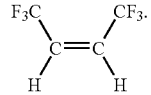

2. The process of claim 1, wherein any of the steps can be run in a continuous manner.

3. The process of claim 1, wherein the compound $CF_3CX=CXH$ is $CF_3CCl=CHCl$.

4. The process of claim 1, wherein the compound $CF_3CX=CXH$ is $CF_3CCl=CFH$.

5. The process of claim 1, wherein the compound $CF_3CXClCXHCCl_3$ is $CF_3CCl_2CHClCCl_3$.

6. The process of claim 1, wherein the compound $CF_3CXClCXHCCl_3$ is $CF_3CCl_2CFHCCl_3$.

7. The process of claim 1, wherein the step (c) reaction comprises dehydrohalogenation of $CF_3CXHCXHCF_3$.

8. The process of claim 1, wherein the step (c) reaction comprises dehalogenation of $CF_3CXHCXHCF_3$.

9. The process of claim 1, wherein the step (c) reaction comprises both dehydrohalogenation and dehalogenation of $CF_3CXHCXHCF_3$.

10. A continuous process for preparing cis-1,1,1,4,4,4-hexafluorobutene comprising steps:
    (a) the addition of $CCl_4$ to $CF_3CCl=CHCl$ using $CuCl_2$ and acetonitrile to produce $CF_3CCl_2CHClCCl_3$;
    (b) the fluorination of $CF_3CCl_2CHClCCl_3$ from step (a) using $SbCl_5$ and anhydrous HF to produce $CF_3CCl_2CHClCF_3$;

(c) the dehydrohalogenation of $CF_3CCl_2CHClCF_3$ from step (b) with KOH and a phase transfer catalyst to produce $CF_3CCl{=}CClCF_3$;
(d) the dehalogenation of $CF_3CCl{=}CClCF_3$ from step (d) with Zn dust and acetic anhydride to produce $CF_3C{\equiv}CCF_3$; and
(e) the reduction of $CF_3C{\equiv}CCF_3$ from step (d) using hydrogen and a catalyst consisting of 5% Pd on $CaCO_3$ poisoned with 3.5% lead, to produce cis-$CF_3CH{=}CHCF_3$.

\* \* \* \* \*